United States Patent [19]

Mulshine et al.

[11] Patent Number: 6,071,949
[45] Date of Patent: *Jun. 6, 2000

[54] USE OF LIPOXYGENASE INHIBITORS AS ANTI-CANCER THERAPEUTIC AND INTERVENTION AGENTS

[75] Inventors: James L. Mulshine, Bethesda, Md.; Marti Jett, Washington, D.C.

[73] Assignee: The United States of America as represented by the Department of Health and Human Services, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/704,569

[22] PCT Filed: Mar. 14, 1995

[86] PCT No.: PCT/US95/03337

§ 371 Date: Dec. 3, 1996

§ 102(e) Date: Dec. 3, 1996

[87] PCT Pub. No.: WO95/24894

PCT Pub. Date: Sep. 21, 1995

[51] Int. Cl.[7] .................................................. A61K 31/40
[52] U.S. Cl. ............................................ 514/418; 514/419
[58] Field of Search ......................................... 514/418, 419

[56] References Cited

U.S. PATENT DOCUMENTS

| | | | |
|---|---|---|---|
| 5,010,080 | 4/1991 | Fuller et al. | 514/255 |
| 5,030,642 | 7/1991 | Fuller et al. | 514/357 |
| 5,093,351 | 3/1992 | Batt | 514/415 |
| 5,182,367 | 1/1993 | Gillard et al. | 530/350 |

FOREIGN PATENT DOCUMENTS 0 275 667 B1  7/1988  European Pat. Off. .

OTHER PUBLICATIONS

Carter et al. Chemotherapy of Cancer 2nd Ed John Wiley & Sons, N.Y., N.Y p. 364, 1981.

*Primary Examiner*—Jerome D. Goldberg
*Attorney, Agent, or Firm*—Morgan & Finnegan, L.L.P.; William S. Feiler; Dorothy R. Auth

[57] ABSTRACT

The present method provides a method for treating an epithelial cell-derived cancer in a subject in need of such treatment which comprises administering to the subject an amount of a 5-lipoxygenase inhibitor or derivative thereof effective to treat the epithelial cell-derived cancer. The present invention also provides a method for preventing an epithelial cell-derived cancer in a subject in need of such prevention which comprises administering to the subject an amount of a 5-lipoxygenase inhibitor effective to prevent the epithelial cell-derived cancer. Suitable 5-lipoxygenase inhibitors useful for the methods of the present invention preferably include 2-(12-Hydroxydodeca-5,10-dinyl)-3,5,6-trimethyl-1,4-benzoquinone and derivatives thereof; Nordihydroguaiaretic acid and derivatives; and 3-[1-(4-chlorobenzyl)-3-t-butyl-thio-t-isopropyl-indol-2-yl]-2-2-dimethylpropanoic acid and derivatives thereof. Also intended to be encompassed by this invention are hydroxyurea derivatives as inhibitors of 5-lipoxygenase inhibitors for use in the prevention and treatment of epithelial cell-derived cancers.

12 Claims, 11 Drawing Sheets

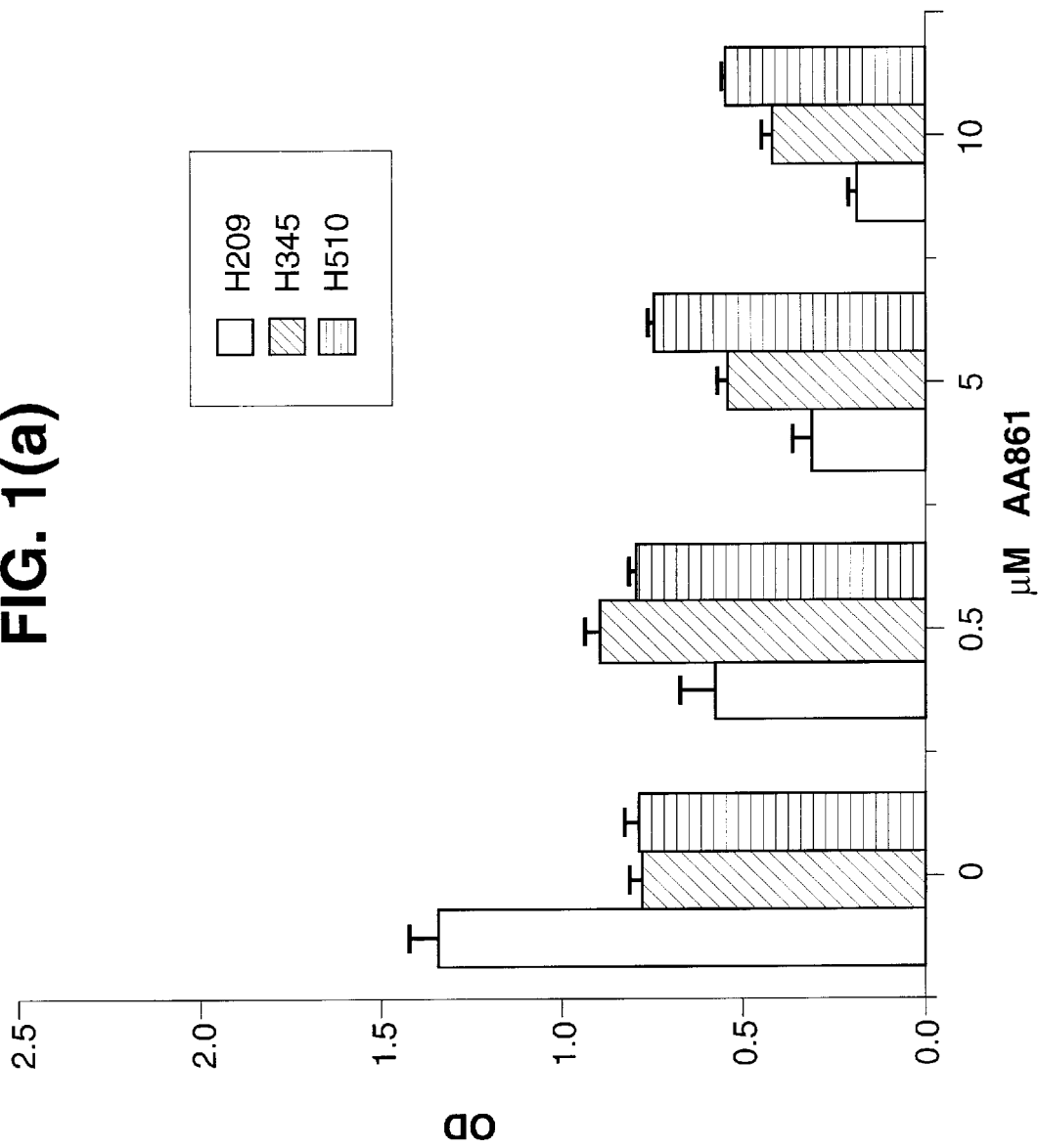

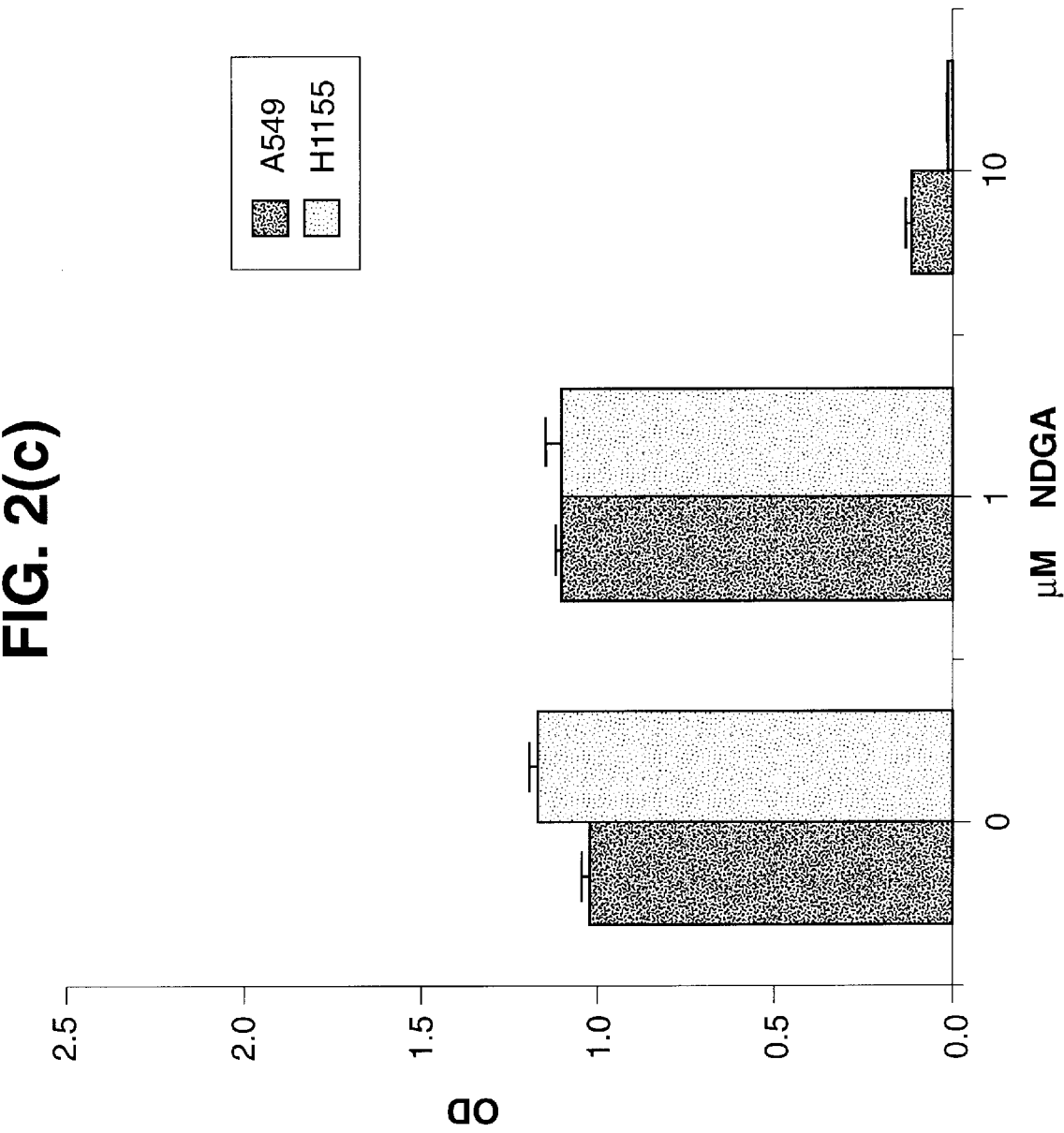

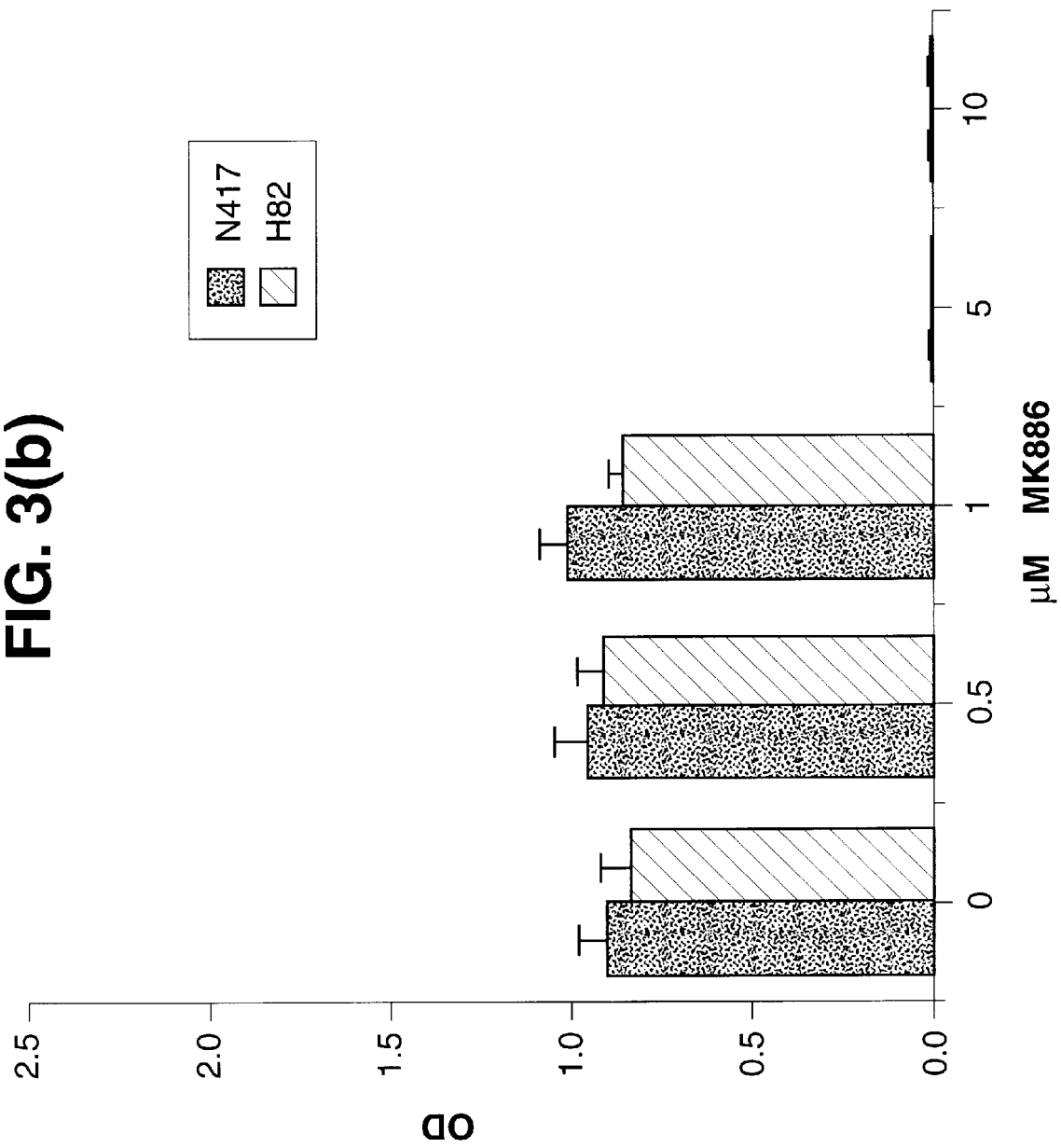

USE OF LIPOXYGENASE INHIBITORS AS ANTI-CANCER THERAPEUTIC AND INTERVENTION AGENTS

This application is a 371 of PCT/US 95/03337 filed on Mar. 14, 1995.

FIELD OF THE INVENTION

This invention is in the field of the prevention and treatment of cancer. More specifically, this invention relates to the use of 5-lipoxygenase inhibitors or derivatives thereof in preventing and treating cancer.

BACKGROUND OF THE INVENTION

Arachidonic acid (AA) is a 20-carbon polyunsaturated fatty acid derived from dietary sources. Oxygenated AA metabolites participate in a variety of biologic and pathological processes including inflammation, bronchial asthma, and shock. Activation of AA metabolism is initiated by the release of AA from the phospholipid pool by the action of enzymes or other mediators. The released AA can be metabolized by either the lipoxygenase pathway where AA is converted by fatty acid lipoxygenases into hydroperoxy derivatives, giving rise to leukotrienes, or the cycloxygenase pathway where a fatty acid transforms AA rapidly to the prostaglandin $PGG_2$, which in turn is further converted enzymatically.

A protein designated 5-lipoxygenase activating protein (FLAP) appears to be necessary for cellular leukotriene synthesis (U.S. Pat. No. 5,182,367; Miller et al. (1990) *Nature* 343:278–281). FLAP appears to be involved in the translocation of 5-lipoxygenase from the cytosol to the membrane. Other enzymes involved with the sequential metabolism of the lipoxygenase product need to be in close relationship to the 5-lipoxygenase FLAP complex. FLAP and molecules of related structure may be essential to the activity of enzymes in the 5-lipoxygenase pathway as well as the other downstream enzymes required for leukotriene biosynthesis.

Inhibitors of the AA 5-lipoxygenase pathway have shown promise in the treatment of inflammation, asthma, and shock, with minimal side effects in pre-clinical and clinical trials (Batt, *Prog. Med. Chem.* 29:1–63 (1992); Larson, *Ann. Pharmacother.* 27:898–903 (1993)). However, their use for treating or preventing cancer has never been described.

The present invention is directed to the use of inhibitors of 5-lipoxygenase functional activity for the treatment and prevention of epithelial cell-derived cancers. The present invention is also directed to the use of inhibitors of other enzymes in the lipoxygenase pathway involved in the metabolism of AA for use in the treatment and prevention of epithelial cell-derived cancers.

SUMMARY OF THE INVENTION

In general the present invention relates to the use of lipoxygenase inhibitors in therapeutic applications, in particular to the prevention and treatment of epithelial cell-derived cancers.

It is an object of the present invention to provide a method for treating an epithelial cell-derived cancer in a subject in need of such treatment which comprises administering to the subject an inhibitor of a 5-lipoxygenase enzymatic function or a downstream leuketriene synthetic enzyme effective to treat the epithelial cell-derived cancer.

It is also an object of the present invention to provide a method for preventing an epithelial cell-derived cancer in a subject in need of such prevention which comprises administering to the subject an inhibitor of a 5-lipoxygenase enzymatic function or other downstream leuketriene synthetic enzyme effective to prevent the epithelial cell-derived cancer.

It is yet another object of the present invention to provide a method for preventing an epithelial cell-derived cancer in a subject in need of such prevention which comprises administering to the subject an amount of an inhibitor of an enzyme that metabolizes arachidonic acid effective to prevent an epithelial cell derived cancer.

It is a further object of the present invention to provide a method for treating an epithelial cell derived cancer in a subject in need of such treatment which comprises administering to the subject an amount of an inhibitor of an enzyme that metabolizes arachidonic acid effective to treat the epithelial cell-derived cancer.

It is also another object of the invention to provide a method for treating an epithelial cell derived cancer in a subject in need of such treatment which comprises administering to the subject an amount of a hydroxyurea derivative effective to treat the epithelial cell derived cancer.

It is an object of this invention to provide a method for preventing an epithelial cell derived cancer in a subject in need of such prevention which comprises administering to the subject an amount of a hydroxyurea derivative effective to treat the epithelial cell derived cancer.

It is yet another object of this invention to provide pharmaceutical compositions to use on the methods described herein.

BRIEF DESCRIPTION OF THE FIGURES

FIG. 1(*a*): classic SCLC cell lines NCI-H209, NCI-H345, and NCI-H57201 10. FIG. 1(*b*): variant SCLC cell lines NCI-N417 and NCI-H82. FIG. 1(*c*): NSCLC cell lines NCI-H23, A549, and NCI-H1155.

FIG. 2(*a*): classic SCLC cell lines NCI-H209 and NCI-H345. FIG. 2(*b*): variant SCLC cell lines NCI-N417 and NCI-H82. FIG. 2(*c*): NSCLC cell lines A549 and NCI-H1155.

FIG. 3(*a*): classic SCLC cell lines NCI-H209 and NCI-H345. FIG. 3(*b*): variant SCLC cell lines NCI-N417 and NCI-H82. FIG. 3(*c*): NSCLC cell lines A549 and NCI-H1155.

DETAILED DESCRIPTION OF THE INVENTION

Figure 1B:
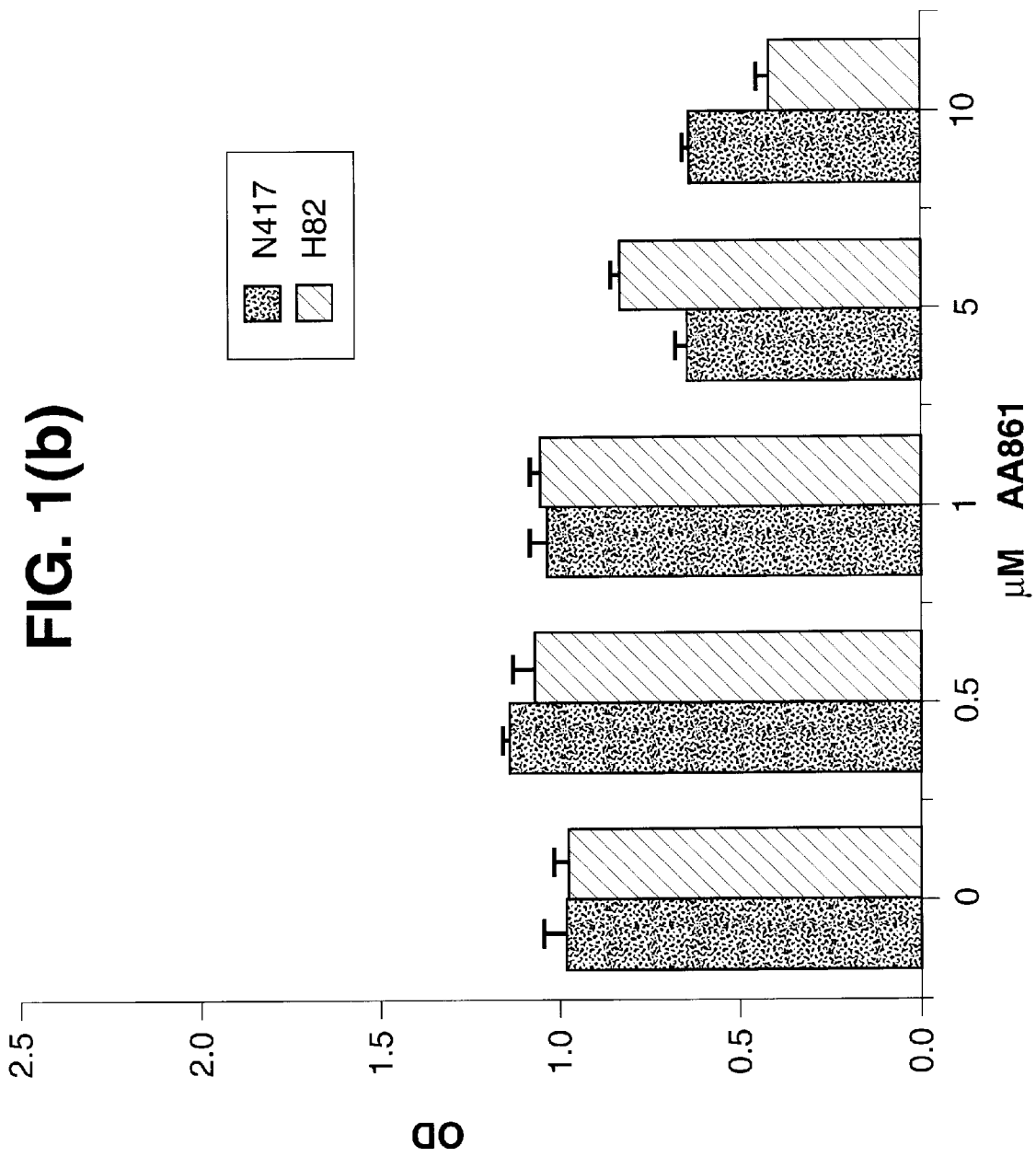
FIGS. 1(*a*), 1(*b*), and 1(*c*). Effect of 5-lipoxygenase inhibitor AA861 on the in vitro growth of specific lung cancer cell lines.

The present invention provides a method for treating or preventing an epithelial cell-derived cancer in a subject in need of such treatment or prevention which comprises administering to the subject an amount of a 5-lipoxygenase inhibitor or derivative thereof, effective to treat or prevent the epithelial cell-derived cancer. The present invention also provides a method for treating or preventing an epithelial cell derived cancer in a subject in need of such treatment by administering an effective amount of an inhibitor of other enzymes involved in the metabolism of arachidonic acid in the 5-lipoxygenase pathway which comprises administering to the subject an amount of the inhibitor effective to treat or prevent a epithelial cell derived cancer.

The term "treatment" includes partial or total inhibition of the cancer growth, as well as partial or total destruction of the cancer cells.

The term "prevention" includes either preventing the onset of clinically evident cancer altogether or preventing the onset of a preclinically evident stage of cancer in individuals at risk, also intended to encompassed by this definition is the prevention of initiation for malignant cells or to arrest or reverse the progression of premalignant cells to malignant cells.

In both methods above, the epithelial cell-derived cancer (epithelial carcinoma) includes basal cell carcinoma, adenocarcinoma, colon cancer, prostate cancer, renal cell carcinoma, and other known cancers that effect epithelial cells throughout the body. Preferably, the epithelial cell-derived cancer is lung cancer or breast cancer.

The term "subject" for purposes of treatment includes any human or animal subject who has any one of the known epithelial cell-derived cancers, and preferably is a human subject. For methods of prevention, the subject is any human or animal subject, and preferably is a human subject who is at risk for obtaining an epithelium cell-derived cancer. The subject may be at risk due to exposure to carcinogenic agents, being genetically predisposed to have the cancer, and the like.

Inhibitors of the 5-lipoxygenase pathway in the metabolism of arachidonic acid used in the prevention and treatment of epithelial cell derived cancers may inhibit enzyme activity through a variety of mechanisms.. By the way of example, the inhibitor may block or reverse the association of the enzyme with the membrane or inhibit the translocation of specific enzymes such as 5-lipoxygenase via a protein such as FLAP. Alternatively, the inhibitors used in the methods described herein may block the enzyme activity directly by acting as a substrate for the enzyme or by depriving the enzyme of necessary cofactors.

The methods provided herein relate to the use of 5-lipoxygenase inhibitors or derivatives thereof in the prevention and treatment of epithelial cell derived cancers. In the preferred embodiments, the 5-lipoxygenase inhibitor is 2-(12-Hydroxydodeca-5,10-diynyl)-3,5,6-trimethyl-1,4-benzoquinone (AA861) (Yoshimoto, et al. (1982) *Biochemical Biophysica ACTA* 713:470–473; Ashida, Y, et al. (1993) *Prostoglandins* 26(6):955) or derivatives thereof; Nordihydroguaiaretic acid (NDGA) (Wang, et al. (1991) *Mutation Research* 261:153–162; Salari, et al. (1984) *Prostoglandins Leukotrienes And Medicine* 13:53–60) or derivatives thereof; or 3-[1-(4-chlorobenzyl)-3-t-butyl-thio-5-isopropylindol-2-yl]-2, 2-dimethylpropanoic acid (MK886) (Gillard et al. (1989) *Can J. Physiol. Pharmacol* 67:456–464; Rouzer, et al (1990) *Journal of Biological Chemistry* 265:1436–1442) or derivatives thereof.

Derivatives are intended to encompass any compounds which are structurally related to AA861, NDGA or MK886 or which possess the substantially equivalent biologic activity of AA861, NDGA or MK886. By way of example, such inhibitors may include, but are not limited to, derivatives which act as co-factor antagonist, better enzymatic substrates or inhibitors of activating peptide function.

MK886 as used herein has the formula:

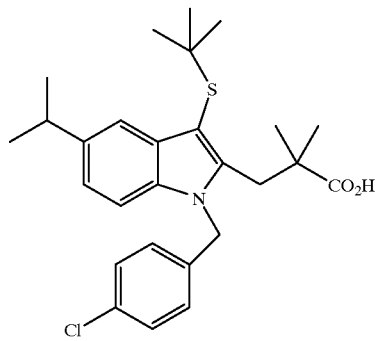

Derivatives of MK886 are also intended to be encompassed by this invention. In a preferred embodiment a derivative of MK886 may have the general formula:

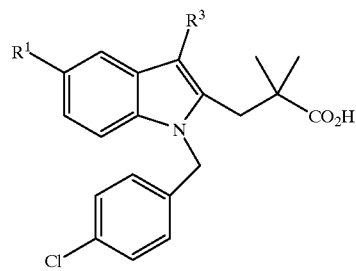

Wherein $R^1$ is $C_1-C_6$ alkyl or OH or $R^2CO$— in which $R^2$ is H or $C_1-C_6$ alkyl or quinoline or a long chain hydrocarbon possessing 1–32 carbon atoms and 0–6 double bonds. Examples of long chain hydrocarbons include, but are not limited to, linoleic acid (18:2) or oleic acid (18:1). Wherein $R^3$ is $C_1-C_6$ alkyl or $R^4S$— or $R^5SO$— or $R^6SO_2$— and which $R^4$ or $R^5$ or $R^6$ may be $C_1-C_6$ alkyl or quinoline or a long chain hydrocarbon possessing 1–32 carbon atoms and 0–6 double bonds. Examples of long chain hydrocarbon include, but are not limited to, linoleic acid (18:2) or oleic acid (18:1).

Examples of $R^3$ include, but are not limited to, t-butyl thio, cyclic propyl methylthio, phenyl sulfonyl, phenyl, methyl, phenylthiol.

Figure 5:
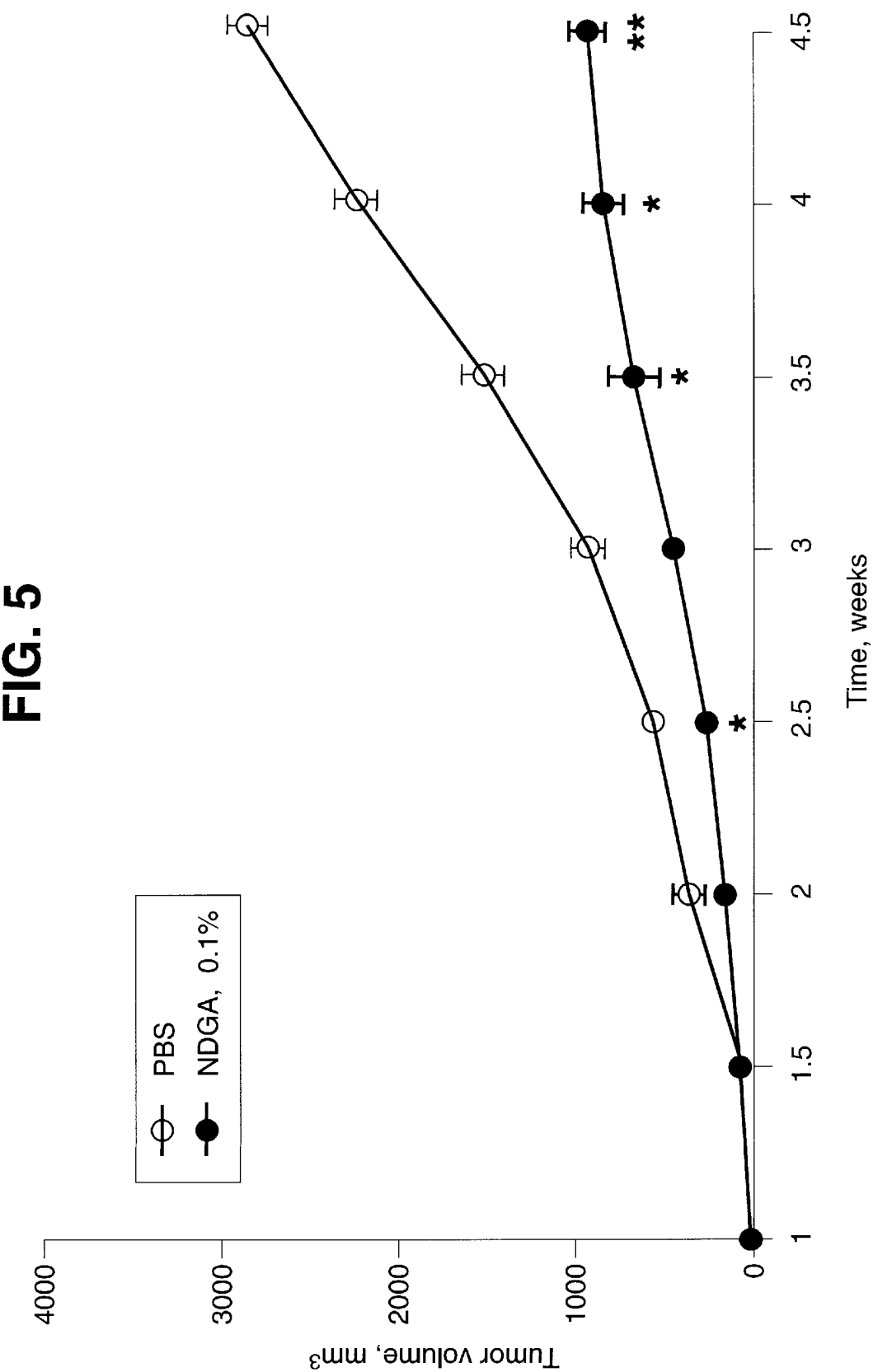
FIG. 5. Effect on tumor volume (NCI-H209 xenografts) over time in animals treated with NDGA (●) and control animals receiving phosphate buffered saline (PBS;O)

Derivatives of MK886 intended to be encompassed by this invention include, but are not limited to, L-669,572, 3-[1-(p-cholorobenzyl)-5-isopropyl-3-cyclopropylmethylthioindole-2-yl]-2,2-dimethylpropanoic acid; L-663,511 3-[1-(p-cholorobenzyl)-5-isopropyl-3-phenysulfonylindol-2-yl)-2,2-dimethylpropanoic acid, L-665,210, 3-[1-(p-chlorobenzyl)-5-isopropyl-3-phenysulfonylindol-2-yl)-2,2-dimethylpropanoic aid; L-654-639, 3[1-(p-chlorobenzyl)-5-methoxy-3-methylindol-2-yl]-2,2-dimethylpropanoic acid; and L-668, 017 described in Rouzer et al. (1990) *Journal of Biological Chemistry* 265:1436–1442 which is herein incorporated by reference (FIG. 5). In a preferred embodiment, the MK886 derivative is 3-(1-(4-chlorobenzyl)-3-(1-butyl-thio)-5-(quinolin-2-yl-methoxy)-indol-2-yl)-2,2-dimethyl propanoic acid) (MK-591) (Tagari, et al. (1993) *Agents Action* 40:62–71).

In yet another embodiment of this invention hydroxyurea derivatives are also used as inhibitors of 5-lipoxygenase in the prevention and treatment of epithelial cell derived cancers. Examples of hydroxyurea derivatives include, but are not limited to, (N-(1-benzo(b)thien-2-ylethyl)-N-hydroxyurea) (zileuton) (Tagari, et al. (1993) *Agents Action* 40:62–71 herein incorporated by reference.

In an alternative embodiment of this invention inhibitors of other enzymes that metabolize arachidonic acid downstream of 5-lipoxygenase, may also be used to prevent or treat epithelial cell derived cancers in a subject in need of such treatment in a method which comprises administering to the subject an amount effective to prevent or treat the epithelial cell derived cancer. Such inhibitors may effect the activity of the enzyme either directly by acting as a substrate inhibitor or by depriving the enzyme of a cofactor. The inhibitor may also act by targeting proteins such as FLAP which are responsible for the translocation of the enzymes to the membrane where the enzymes are activated.

The compounds utilized in the methods of the present invention may be present in the form of free bases or pharmaceutically acceptable acid addition salts thereof. Examples of suitable acids for salt formation are: methanesulfonic, sulfuric, hydrochloric, phosphoric, acetic, citric, lactic, ascorbic, maleic, and the like.

The administration for the above methods may be affected by means known to those skilled in the art such as oral, rectal, topical (including aerosol), intranasal, intravenous, subcutaneous, intramuscular, intrabronchial, intracavitary, or intraperitoneal routes of administration. If the cancer is localized, local administration rather than system administration is preferred. Formulation in a lipid vehicle may be used to enhance bioavailability.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For oral administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

If the cancer is localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol exipients, such as saline, and administered using commercially available nebulizers. Formulation in a fatty acid source may be used to enhance biocompatibility. Aerosol delivery is the preferred method of delivery for epithelial cancers of the lung for prevention application.

For rectal administration, the active ingredient may be formulated into suppositories using bases which are solid at room temperature and melt or dissolve at body temperature. Commonly used bases include coca butter, glycerinated gelatin, hydrogenated vegetable oil, polyethylene glycols of various molecular weights, and fatty esters of polyethylene stearate.

The dosage form and amount can be readily established by reference to known cancer treatment or prophylactic regiments. The dosage for the inhibitors or derivatives thereof may be from about 0.1 ng/kg to about 450 mg/kg, most preferred is about 0.5 ng/kg to about 100 mg/kg, and most preferably is about 1 ng/kg to about 10 mg/kg. The serum concentration of the inhibitor may be from about 1 $\mu$g/ml to about 20 $\mu$g/ml. The actual dose will depend upon whether the administration is for treatment or prophylactic purposes, the route of administration, the location of the cancer, as well as the pharmacokinetic properties of the individual treated. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual.

The administration of the present invention may be for either prevention or treatment purposes. The methods and compositions used herein may be used alone or in conjunction with additional therapies known to those skilled in the art in the prevention or treatment of cancer. Alternatively, the methods and compositions described herein may be used as adjunct therapy. By way of example, the 5-lipoxygenase inhibitor may be administered alone or in conjunction with other antineoplastic agents or other growth inhibiting agents or other drugs or nutrients. Alternatively the 5-lipoxygenase inhibitor or derivatives thereof and the inhibitor of other downstream enzymes involved in the metabolism of arachidonic acid may be administered in combination with each other.

In an alternative embodiment molecular methods may be used to inhibit the 5-lipoxygenase. By way of example antisense constructs generated by methods known to those skilled in the art can be used to target the messenger RNA of the 5-lipoxygenase enzyme.

All books, articles or patents reference herein are incorporated by reference. The present invention is described in the following Experimental Details section, which sets forth specific examples to aid in an understanding of the invention, and should not be construed to limit in any way the invention as defined in the claims which follow thereafter.

EXAMPLE 1

Materials and Methods

Cell lines: The following cell lines were used: classic small cell lung cancer (SCLC) cell lines NCI-H209, NCI-H345, and NCI-H510; variant SCLC cell lines NCI-N417 and NCI-H82; large cell carcinoma cell line NCI-H1155; adeno carcinoma cell line NCI-H23; and bronchioalveolear carcinoma cell line A549, breast cancer cell line MCF-7

(American Type Tissue Culture Rockville Md.; ATCC) and a colon cancer cell line NCI-H630 (ATCC). All cells were grown in RPMI-1640, supplemented with 5% fetal bovine serum (FBS), penicillin and streptomycin (Gibco, Grand Island, N.Y.), and were maintained in a 5% $CO_2$ atmosphere at 37° C. All cell lines were free of mycoplasma contamination.

Biochemical compounds: General lipoxygenase inhibitor Nordihydroguaiaretic acid (NDGA) and 5-lipoxygenase inhibitor AA861, are readily commercially available and were purchased from Biomol Research Laboratories (Plymouth Meeting, Pa.). 5-lipoxygenase inhibitor MK886 and MK-591 were obtained from Merck Frost. MK886 may be synthesized as described in Gillard, J., et al. *Can. J. Physiol. Pharmacol.* 67:456–464 (1989)).

Growth studies: A modification (Promega CellTiter 96®, Promega Madison, Wis.) of the semiautomated colorimetric assay, MTT (Nakanishi, et al. *Exper. Cell Biol.* 56:74–85 (1988)), which quantitates cell numbers based on reduction of a tetrazolium compound by tumor cells as determined by a spectrophotometer (540 nm) was used. All assays were performed in RPMI-1640 media supplemented with transferrin (T) 10 µg/ml, insulin (I) 5 µg/ml and selenium (S) $5 \times 10^8 M$ (TIS) (Sigma Chemicals, St. Louis, Mo.). Seeding densities were $1-2 \times 10^4$ cells/well, and cells were grown for 5 days. Each experiment was reported as mean optical density corrected for background =/− standard deviation for a minimum of six data points per experiment, with each experiment repeated at least three times.

RESULTS

Figure 1C:
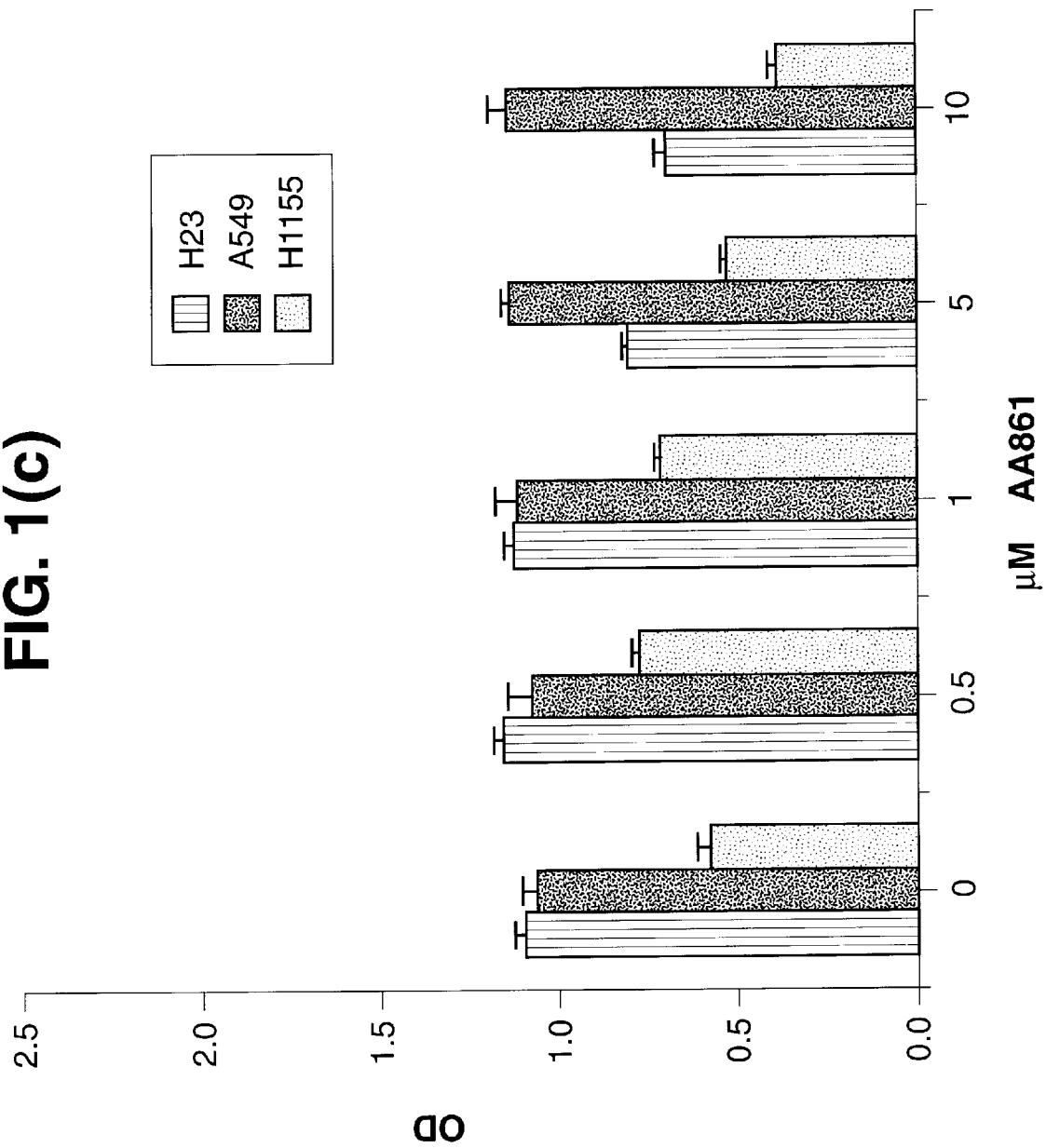
Figure 2A:
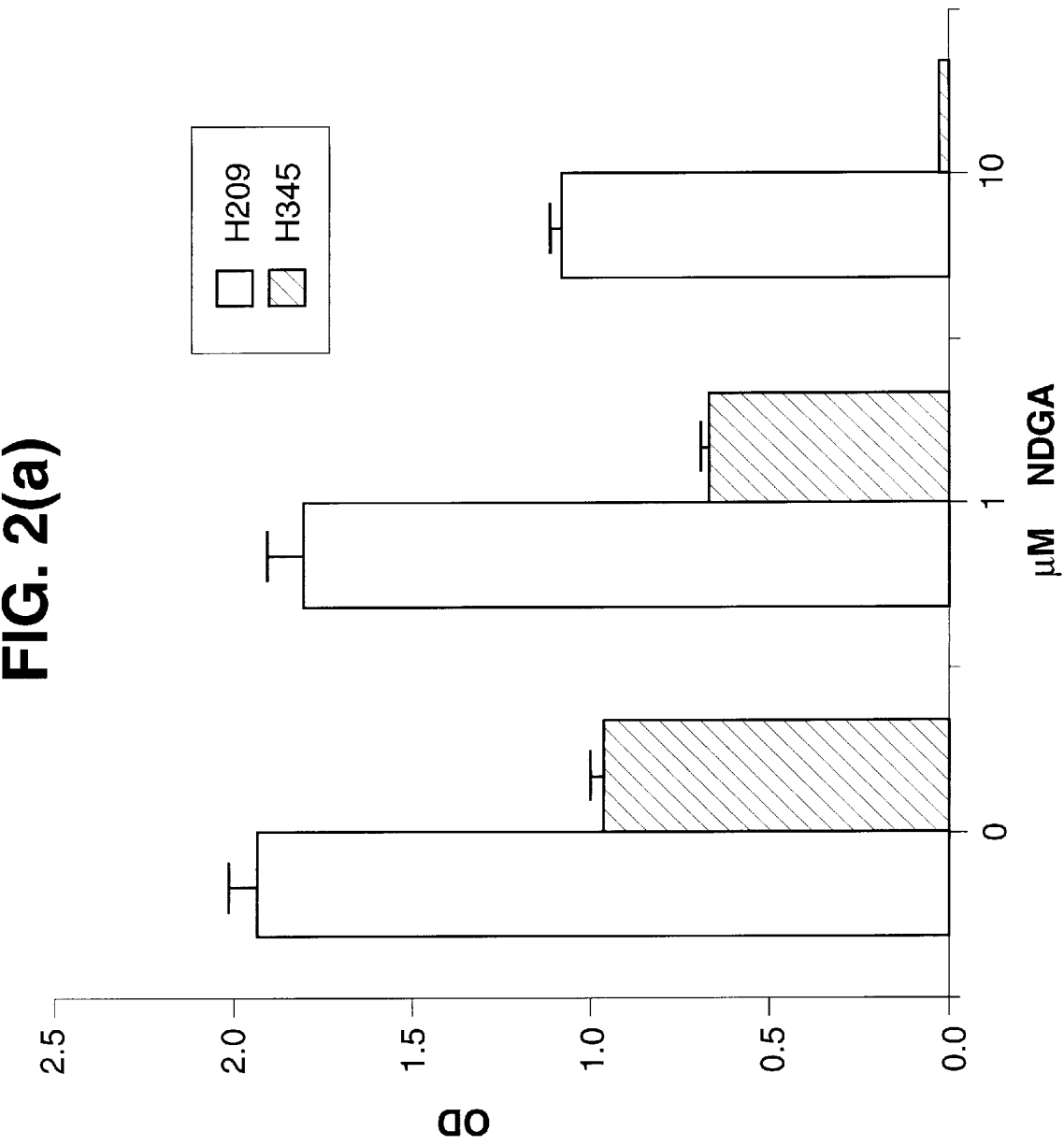
FIGS. 2(*a*), 2(*b*), and 2(*c*). Effect of 5-lipoxygenase inhibitor NDGA on the in vitro growth of lung cancer cell lines.
Figure 2B:
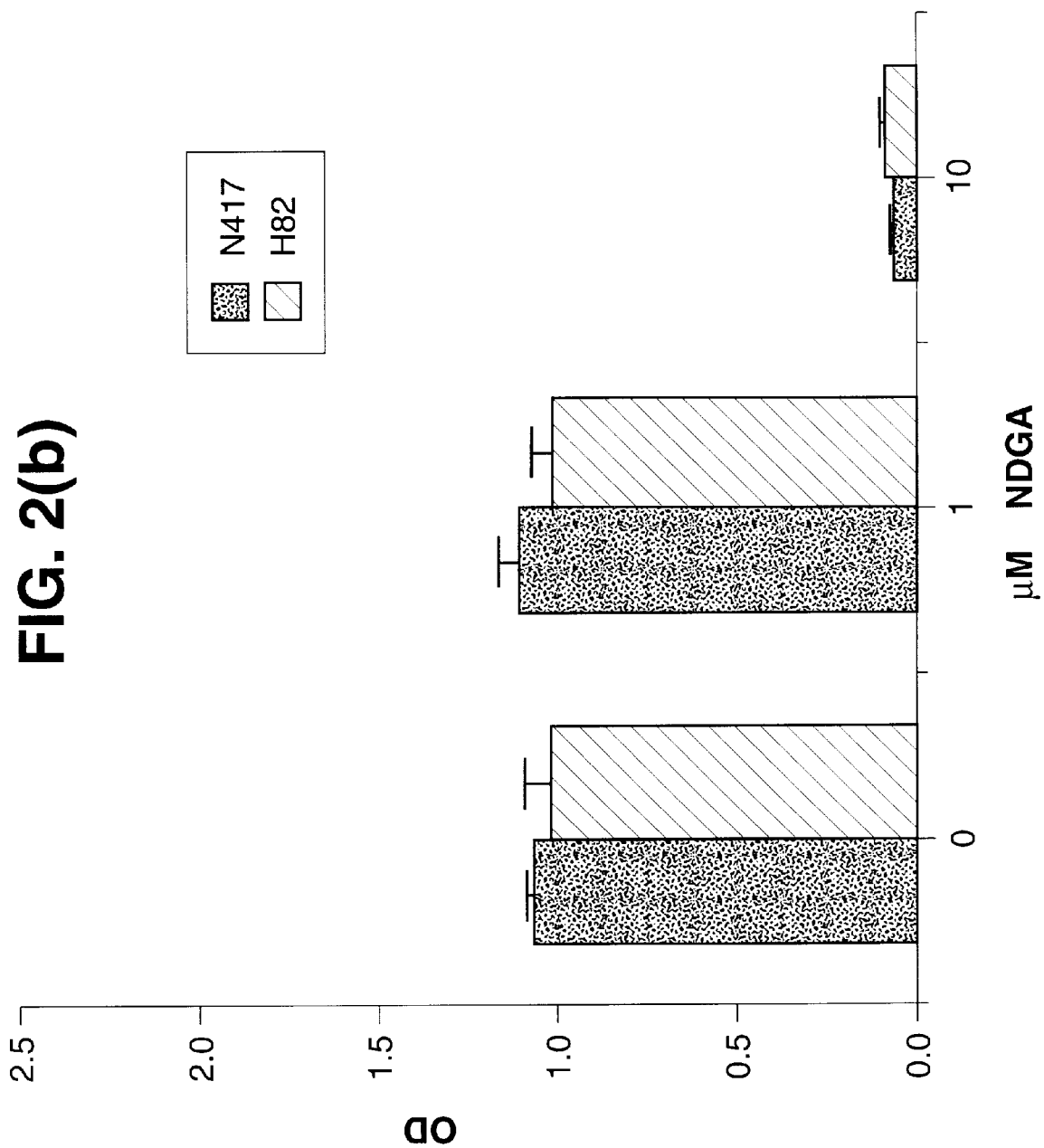
Figure 3A:
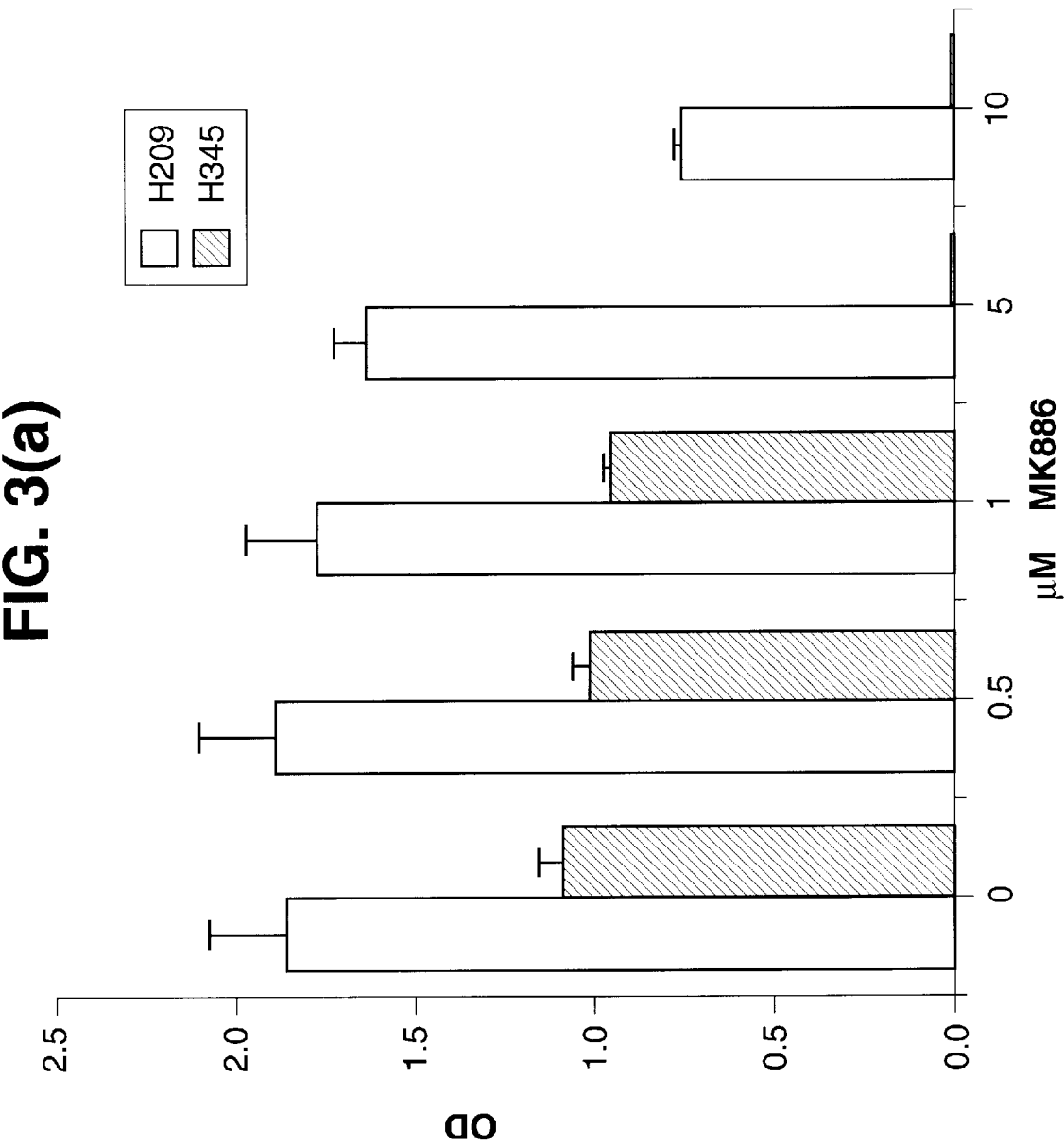
FIGS. 3(*a*), 3(*b*), and 3(*c*). Effect of 5-lipoxygenase inhibitor MK-886 on the in vitro growth of lung cancer cell lines.
Figure 3C:
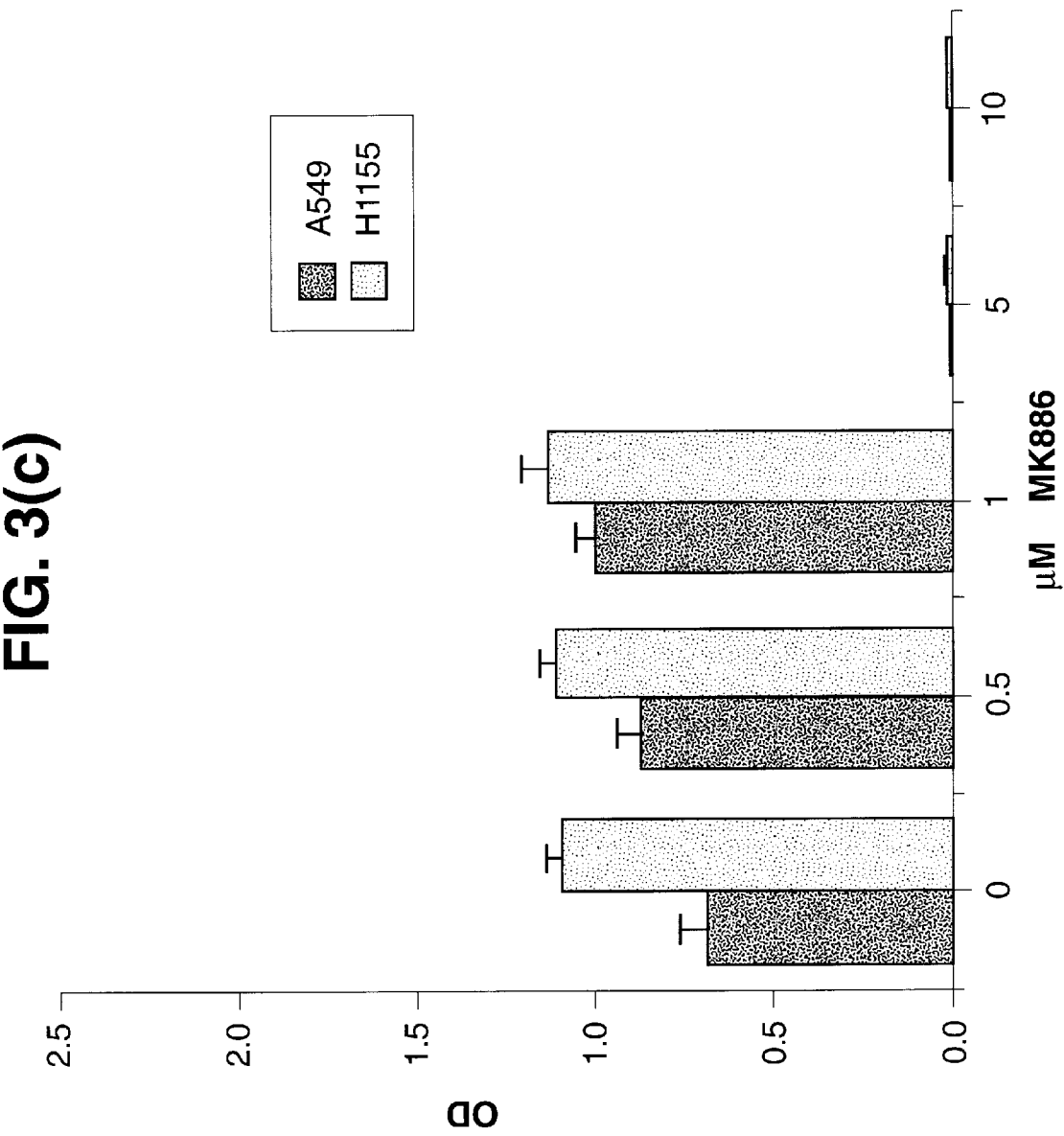
Figure 4:
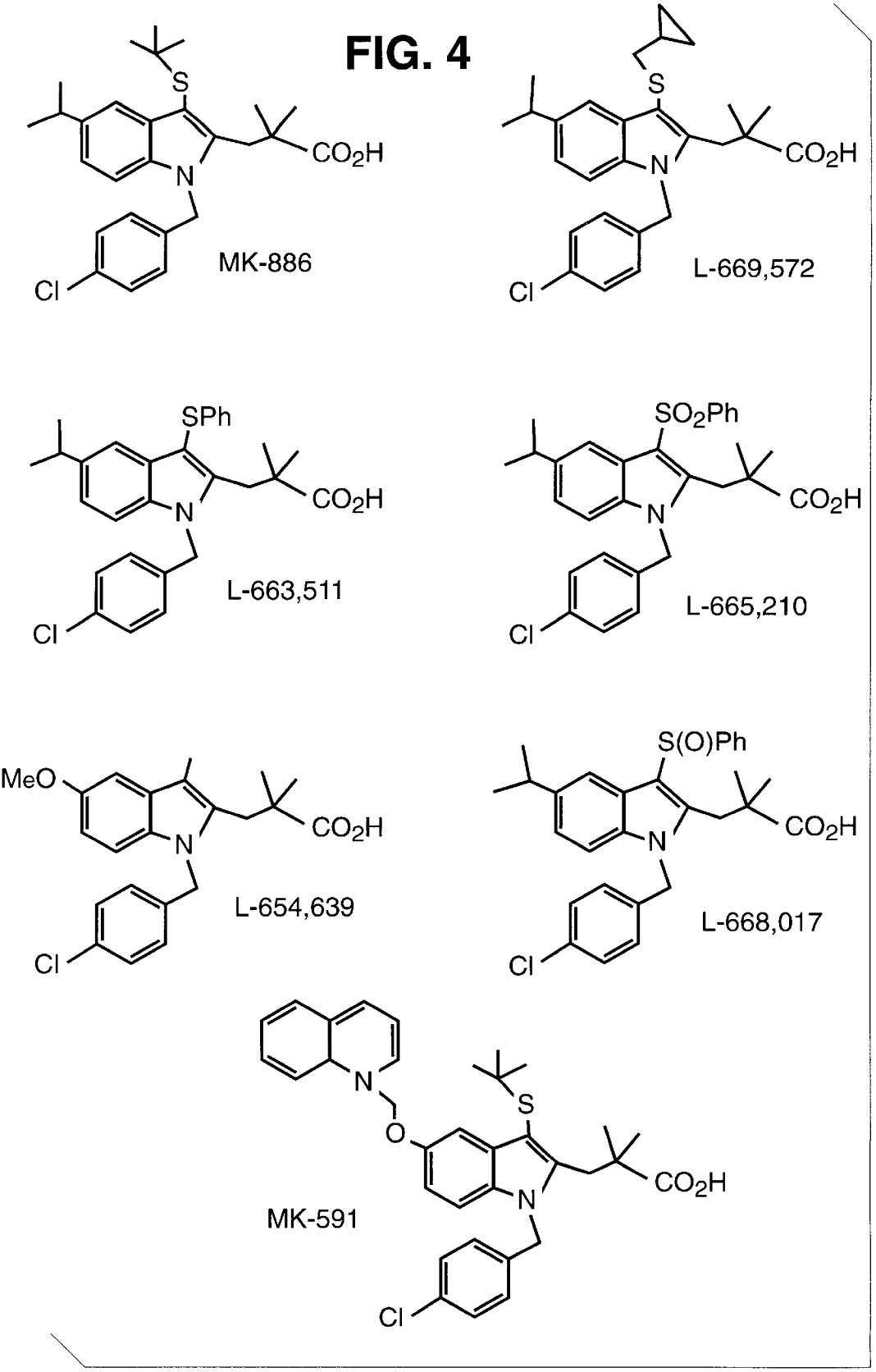
FIG. 4. Structures of MK-886 and related structures: L-669,572, L-663,511, L-665,210, L-654,639, L-668,017 and MK-591.

AA861 was tested in a dose range of 0.5–10 µM on three classic SCLC cell lines, two variant SCLC cell lines, and three NSCLC cell lines. The effect of AA861 on the in vitro growth of the specific lung cancer cell lines is presented in FIGS. 1(*a*), 1(*b*), and 1(*c*). AA861 significantly inhibited growth on all of the SCLC cell lines, and two out of three of the NSCLC cell lines. A bronchioalveolear carcinoma, A549, was repeatedly resistant to AA861. The reason for this resistance is unclear. NDGA also was tested on four SCLC cell lines and two NSCLC cell lines, and the results are presented in FIGS. 2(*a*), 2(*b*), and 2(*c*). NDGA inhibited the growth of all of the lung cancer cell lines tested. MK886 also was tested on four SCLC cell lines and two NSCLC cell lines, and the results are presented in FIGS. 3(*a*), 3(*b*), and 3(*c*). MK886 showed similar inhibition results as NDGA. AA861 inhibited growth of MCF-7 cells relative to controls (absence of AA861) to 70% and H630 to 50%. NDGA inhibited growth of MCF-7 cells relative to controls 80% and H630 cells 50% relative to controls. MK886 inhibited growth of MCF7 cells 100% relative to controls.

EXAMPLE 2

In Vivo Models of Cancer and Carcinogeneses

The therapeutic potential of the 5-lipoxygenase inhibitor, NDGA, was assessed in a heterotransplant animal model. Using conventional methodology small cell lung cancer cells (cell line NCI-209) were transplanted into nude mice. Experimental animals received a 0.1% solution of NDGA in water ad libitum and drank about 5 cc of water/day. Control animals received phosphate buffered saline. The xenografts of the small cell lung cancer line, NCI-209, showed a significant reduction in heterotransplant size (compared to controls) at 2.5 to 4.5 weeks after cell line engraftment in mice receiving orally administered NGDA. (see FIG. 5 and Table I)

TABLE I

| | Weight of nude mice (grams) | |
|---|---|---|
| Treatment | Mouse | Tumor |
| None | 26.5 ± 1.3 | 1.29 ± 0.07 |
| NDGA | 25.9 ± 1.9 | 0.60 ± 0.19* |

The mean weight ± S.D. of 4 determinations is indicated; $p < 0.05$, * using students t-test.

AA861 and derivatives thereof and MK886 and derivatives thereof may be also be tested in the heterotransplant model. Suggested serum concentration of the inhibitor in experimental animals may be from about 1 µg/ml to about 20 µg/ml. In addition to treatment models, in vivo models of cancer prevention may also be assessed for the therapeutic potential of the inhibitors or derivatives thereof.

All publications mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for treating an epithelial cell-derived cancer in a subject sensitive to an inhibitor, which comprises, administering to the subject an amount of the inhibitor, effective to treat the epithelial cell derived cancer said inhibitor comprising:

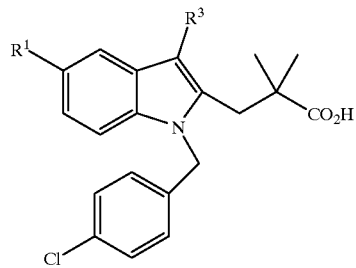

wherein:
$R^1$ is $C_{1-C6}$ alkyl;
$R^3$ is $R^4S$— or $R^5SO$— or $R^6SO2$—; and
$R^4$, $R^5$ and $R^6$ is $C_1-C_6$ alky.

2. The method of claim 1, wherein the inhibitor is 3-[1-(4-chlorobenzyl)-3-t-butyl-thio-t-isopropyl-indol-2-yl]-2,2-dimethylpropanoic acid or derivative thereof.

3. The method of claim 2, wherein the cancer is lung cancer.

4. The method of claim 1, wherein the epithelial cell-derived cancer is lung cancer, colon cancer, or breast cancer.

5. The method of claim 1, wherein the administration is affected by oral, rectal, topical, aerosol, intravenous, subcutaneous, intramuscular, intrabronchial, intracavitary, or intraperitoneal administration.

6. The method of claim 1, wherein the amount is between about 1 ng/kg and about 10 mg/kg.

7. A method for preventing the onset of an epithelial cell-derived cancer sensitive to an inhibitor in a subject in need thereof which comprises administering to the subject an amount of said inhibitor, effective to prevent the epithelial cell derived cancer, said inhibitor comprising:

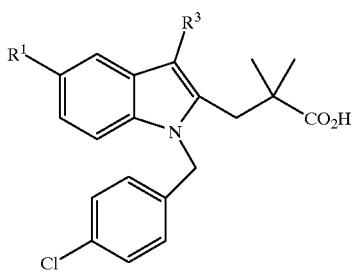

wherein:
$R^1$ is $C_1-C_6$ alkyl;
$R^3$ is $R^4S-$ or $R^5SO-$ or $R^6SO2-$; and
$R^4$, $R^5$ and $R^6$ is $C_1-C_6$ alkyl.

8. The method of claim 7, wherein the inhibitor is 3-[1-(4-chlorobenzyl)-3-t-butyl-thio-t-isopropyl-indol-2-yl]-2,2-dimethylpropanoic acid or derivative thereof.

9. The method of claim 7, wherein the epithelial cell-derived cancer is lung cancer, colon cancer or breast cancer.

10. The method of claim 7, wherein the administration is affected by oral, rectal, topical, aerosol, intravenous, subcutaneous, intramuscular, intrabronchial, intracavitary, or intraperitoneal administration.

11. The method of claim 7, wherein the amount is between about 1 ng/kg and about 10mg/kg.

12. The method of claim 7, wherein the inhibitor is 3-[1-(4-chlorobenzyl)-3-t-butyl-thio-t-isopropyl-indol-2-yl]-2,2-dimethylpropanoic acid or derivative thereof and the cancer is lung cancer.

* * * * *